United States Patent [19]

Haefele

[11] 3,934,002

[45] Jan. 20, 1976

[54] ORAL COMPOSITIONS FOR PLAQUE, CARIES AND CALCULUS RETARDATION WITH REDUCED STAINING TENDENCIES

[75] Inventor: John William Haefele, St. Petersburg, Fla.

[73] Assignee: The Procter & Gamble Company, Cincinnati, Ohio

[22] Filed: Apr. 24, 1974

[21] Appl. No.: 463,495

Related U.S. Application Data

[63] Continuation-in-part of Ser. No. 429,254, Dec. 28, 1973, abandoned, which is a continuation-in-part of Ser. Nos. 338,464, March 6, 1973, and Ser. No. 338,472, March 6, 1973, abandoned, each is a continuation-in-part of Ser. No. 267,816, June 30, 1972, abandoned.

[52] U.S. Cl. .................................................. 424/54
[51] Int. Cl.$^2$ ...................... A61K 7/18; A61K 6/24
[58] Field of Search ............................... 424/49–58, 424/326; 260/565

[56] References Cited

UNITED STATES PATENTS

| | | | |
|---|---|---|---|
| 3,488,419 | 1/1970 | McCune et al. | 424/49 |
| 3,842,168 | 10/1974 | Colodney | 424/52 |

FOREIGN PATENTS OR APPLICATIONS

| | | | |
|---|---|---|---|
| 717,506 | 5/1972 | South Africa | 424/54 |

*Primary Examiner*—Shep K. Rose
*Attorney, Agent, or Firm*—Ronald L. Hemingway; Douglas C. Mohl; Richard C. Witte

[57] ABSTRACT

Oral compositions such as toothpastes, mouthwashes and the like containing a particular substantive -bis-biquanide compound which inhibits the formation of plaque and caries, and an anti-calculus agent which inhibits the tendency of the bis-biguanide compound to produce a stain on oral surfaces.

36 Claims, No Drawings

ORAL COMPOSITIONS FOR PLAQUE, CARIES AND CALCULUS RETARDATION WITH REDUCED STAINING TENDENCIES

REFERENCE TO RELATED APPLICATIONS

This is a continuation-in-part of my copending application, Ser. No. 429,254, filed Dec. 28, 1973 now abandoned, and having the same title; which is a continuation-in-part of my copending application, Ser. No. 338,464, filed Mar. 6, 1973 and having the same title, and Ser. No. 338,472, filed Mar. 6, 1973 and having the same title, now abandoned; all of which are continuations-in-part of Ser. No. 267,816, filed June 30, 1972, also having the same title, now abandoned.

BACKGROUND OF THE INVENTION

The field of this invention is "oral compositions" which term is used herein to designate products which in the ordinary course of usage are retained in the oral cavity for a time and in a manner sufficient to contact essentially all of the dental surfaces, but are not intentionally ingested. Such products include, for example, dentifrices, mouthwashes, prophylaxis pastes and topical solutions.

The bis-biguanide compounds of the present invention are known as effective anti-plaque agents which demonstrate anti-caries activity. However, when compositions containing these compounds are used continuously in a program of oral hygiene, a rather offensive brown stain forms on the oral surfaces which is resistant to removal by ordinary brushing with conventional dentifrices. Thus, prior art compositions containing these bis-biguanide compounds are not cosmetically acceptable. The present invention overcomes this stain problem.

SUMMARY OF THE INVENTION

It has now been discovered that if the specific bis-biguanide compounds disclosed herein and the anti-calculus agents disclosed herein are both used to treat the oral cavity, and especially teeth, either simultaneously or sequentially, the stain that is normally caused by continuous use of the bis-biguanide compounds alone is effectively reduced. When the bis-biguanide compounds and the anticalculus agents are used sequentially, it is preferred that the bis-biguanide material be used first.

DETAILED DESCRIPTION OF THE INVENTION

The bis-biguanide compounds of this invention are known, having been disclosed in U.S. Pat. No. 2,684,924, Rose et al., patented July 27, 1954; U.S. Pat. No. 2,990,425, Senior et al., patented June 27, 1961; U.S. Pat. No. 2,830,006, Burtwell et al., patented Apr. 8, 1958; and U.S. Pat. No. 2,863,019, Buttwell et al., patented Dec. 9, 1958.

The bis-biguanide compounds of this invention have the generic formula:

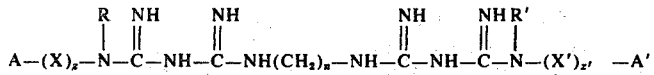

wherein A and A' each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ may optionally be interrupted by oxygen or sulfur atoms, aromatic nuclei, etc. The salts of the above compounds are especially desirable. Water-soluble salts include the acetate, the hydrochloride, and especially the gluconate salt of the above compounds. Water-insoluble salts are disclosed in my copending application, Ser. No. 338,464, filed Mar. 6, 1973, said application also being a continuation-in-part of my application Ser. No. 267,816, filed June 30, 1972, now abandoned. Specific examples of these bis-biguanide compounds are disclosed hereinafter.

The bis-biguanide compounds are normally used in amounts of from about 0.01 to about 2.5% by weight of the composition, preferably from about 0.05 to about 1.2%, and most preferably from about 0.1 to about 0.8%. Depending upon the composition, lesser or greater amounts may be used. In general, all that is required is to have an effective amount of the bis-biguanide salt in the mouth sufficient to give anti-plaque and/or anti-caries effectiveness.

The anti-calculus agent for use in accordance with the present invention is selected from the group consisting of zinc phenolsulfonate, 8-hydroxyquinoline and its pharmaceutically acceptable salts, citric acid and its pharmaceutically acceptable salts, lactic acid and its pharmaceutically acceptable salts, a quaternary ammonium compound selected from the group consisting of N-methyl-N-dodecyl-N-(2-hydroxyethyl)-N-benzyl ammonium chloride, N-methyl-N-(2-hydroxydodecyl)-N-(2-hydroxyethyl)-N-benzyl ammonium chloride, N-methyl-N-(2-hydroxytetradecyl)-N-(2-hydroxyethyl) ammonium chloride, and diisobutylphenoxyethoxy-ethyldimethyl-benzyl ammonium chloride, said quaternary ammonium compounds having been disclosed in U.S. Pat. No. 3,703,583, Nov. 21, 1972, to Donald J. Martin, which is specifically incorporated herein by reference; water-soluble, pharmaceutically acceptable salts of polycarboxylic acids, as disclosed in U.S. Pat. No. 3,308,067, Mar. 7, 1967, to F. L. Diehl, specifically incorporated herein by reference, selected from the group consisting of: (1) water-soluble, pharmaceutically acceptable salts of homopolymers of aliphatic polycarboxylic acids having the following emperical formula:

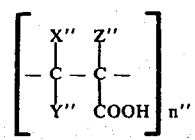

wherein X", Y", and Z" are each selected from the group consisting of hydrogen, methyl, carboxyl, and carboxymethyl; at least one of X", Y" and Z" being selected from the group consisting of carboxy and carboxymethyl, provided that X" and Y" can be carboxymethyl only when Z" is selected from carboxyl and carboxymethyl; wherein only one of X", Y" and Z" can be methyl, and wherein n" is an integer of from 3 to about 5,000, preferably from 4 to about 500; (2) water-soluble pharmaceutically acceptable salts of copolymers of at least two of polycarboxylic acids having the emperical formula of (1); (3) water-soluble, pharmaceutically acceptable salts of copolymers having the following general formula:

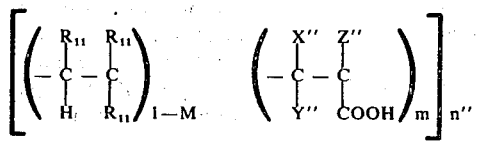

wherein each $R_{11}$ is selected from the group consisting of hydrogen, methyl, carboxyl, carboxymethyl and carboxyethyl; wherein only one $R_{11}$ is methyl; wherein m is at least 45 mole percent of the copolymer; and wherein X", Y", Z" and n" are selected as in (1); polyphosphates of the general formula $H_{a+2}P_aO_{3a+1}$ wherein a in an integer of from 2 to about 30 and the pharmaceutically acceptable salts thereof, for example, monosodium pyrophosphate; pharmaceutically acceptable salts of rare earth metals, such as cerium and lanthanum; phytic acid and the pharmaceutically acceptable salts thereof; and phosphorus containing compounds and the pharmaceutically acceptable salts thereof, selected from the group consisting of compounds of the following general formulae:

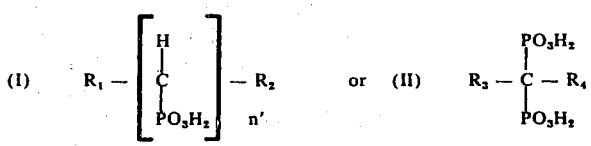

wherein $R_1$ and $R_2$ are hydrogen or $CH_2OH$; n' is an integer of from 3 to 10; $R_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chlorine, bromine, and fluorine), amino, substituted amino (e.g., dimethylamino, diethylamino, N-hydroxyN-ethylamine, acetylamino), $-CH_2COOH$, $-CH_2PO_3H_2$, $-CH(PO_3H_2)(OH)$ or $-CH_2CH(PO_3H_2)_2$; $R_4$ is hydrogen, lower alkyl (e.g., methyl, ethyl, propyl, and butyl), amino, benzyl, halogen (e.g., chlorine, bromine and fluorine), hydroxyl, $-CH_2COOH$, $-CH_2PO_3H_2$, or $-CH_2CH_2PO_3H_2$;

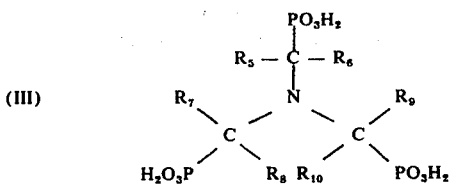

wherein $R_5$, $R_6$, $R_7$, $R_8$, $R_9$ and $R_{10}$ are each hydrogen or lower alkyl;

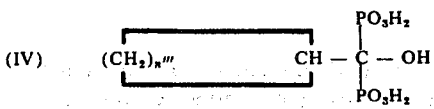

wherein $n'''$ is an integer from 3 to 9;

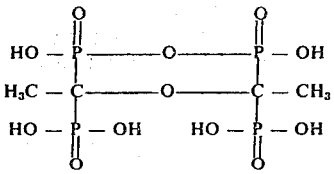

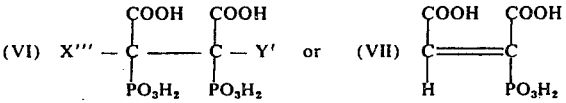

wherein $X''''$ and $Y'$ are each yydrogen and hydroxy; or the condensation products of ammonia and phosphorus pentoxide, e.g.,

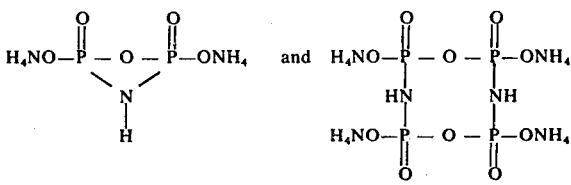

The phosphorus-containing anti-calculus agents are known, having been disclosed in U.S. Pat. No. 3,488,419, H. W. McCune and N. B. Tucker, patented Jan. 6, 1970; U.S. Pat. No. 3,553,314, M. D. Francis, patented Jan. 5, 1971; U.S. Pat. No. 3,553,315, M. D. Francis, patented Jan. 5, 1971; U.S. Pat. No. 3,535,420, H. W. McCune and N. B. Tucker, patented Oct. 20, 1970; U.S. Pat. No. 3,535,421, W. W. Briner and J. S. Widder, patented Oct. 20, 1970; U.S. Pat. No. 3,560,608, W. J. Griebstein, R. J. Grabenstetter and J. S. Widder, patented February 2, 1971; U.S. Pat. No. 3,584,116, M. D. Francis, patented June 8, 1971; and U.S. Pat. No. 3,639,569, R. F. Medcalf, patented Feb. 1, 1972. All of said patents are incorporated herein by reference.

Operable polyphosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane-1,2,3,4,5,6,7,8,9-nonaphosphonic acid; decane-1,2,3,4,5,6,7,8,9,10-decaphosphonic acid and the pharmaceutically acceptable salts of these acids.

Propane-1,2,3-triphosphonic acid and salts thereof can be prepared by a process disclosed in the commonly assigned application of D. Allan Nicholson and Darrel Campbell, Ser. No. 694,002, filed Dec. 27, 1967, now abandoned in favor of Divisional Application Ser. No. 82,819, filed Oct. 21, 1970, referred to in my parent application, Ser. No. 267,816, filed June 30, 1972.

Butane-1,2,3,4-tetraphosphonic acid and salts thereof can be prepared by a process disclosed in the commonly assigned application of D. Allen Nicholson and Darrel Campbell, Ser. No. 694,003, filed Dec. 27, 1967, now abandoned in favor of Divisional Application Ser. No. 67,300, filed Aug. 8, 1970, referred to in my parent application, Ser. No. 267,816, filed June 30,

1972.

The higher aliphatic vicinal polyphosphonates, and salts thereof can be prepared by the process disclosed in U.S. Pat. No. 3,584,035, D. Allan Nicholson and Darrel Campbell, issued June 8, 1971.

Among the operable polyphosphonates encompassed by the above formula (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid; nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-hydroxyethyl)-aminomethanediphosphonic acid; N-acetylaminomethanediphosphonic acid; and aminomethanediphosphonic acid; and the pharmaceutically acceptable salts of these acids.

Operable examples of compounds having formula (III) include: The preferred tris(phosphonoalkyl)amines for the purpose of this invention — tris(phosphonomethyl)amine; tris(1-phosphonoethyl)amine; and tris(2-phosphono-2-propyl)amine; and their pharmaceutically acceptable salts. Tris(phosphonomethyl)amine is especially preferred. The following additional compounds are exemplary of those which can be used herein:

a. bis(phosphonomethyl)-1-phosphonethyl amine;
b. bis(phosphonomethyl)-2-phosphono-2-propyl amine;
c. bis(1-phosphonoethyl)phosphonomethyl amine;
d. bis(2-phosphono-2-propyl)phosphonomethyl amine;
e. tris(1-phosphono-1-pentyl)amine;
f. bis(phosphonomethyl)-2-phosphono-2-hexyl amine; and
g. the pharmaceutically acceptable salts of acids (a) through (f).

Mixtures of any of the foregoing tris(phosphonoalkyl)amines can be used in the compositions of this invention.

Examples of compounds coming within the formula (IV) include the following: Methanecyclobutylhydroxydiphosphonic acid; methanecyclopentylhydroxydiphosphonic acid; methanecyclohexylhydroxydiphosphonic acid; methanecycloheptylhydroxydiphosphonic acid; methanecyclooctylhydroxydiphosphonic acid; methanecyclononylhydroxydiphosphonic acid; methanecyclodecylhydroxydiphosphonic acid; and their pharmaceutically acceptable salts.

Especially preferred methanecycloalkylhydroxydiphosphonates for the purpose of this invention are methanecyclopentylhydroxydiphosphonic acid, methanecyclohexylhydroxydiphosphonic acid, methanecycloheptylhydroxydiphosphonic acid, and the pharmaceutically acceptable salts of these acids.

Examples of cyclic tetraphosphonic acids [formula (V)] include their pharmaceutically acceptable salts.

Operable carboxyphosphonates of the above formula (VI) include ethane-1,2-dicarboxy-1,2-diphosphonic acid; ethane-1,2-dicarboxy-1,2-dihydroxy-1,2-diphosphonic acid; ethane-1,2-dicarboxy-1-hydroxy-1,2-diphosphonic acid; and the pharmaceutically acceptable salts of these acids.

Among the operable carboxyphosphonates encompassed by the above formula (VII) are ethene-1,2-dicarboxy-1-phosphonic acid; and the pharmaceutically acceptable salts of this acid. While the above formula (VII) is representative of cis-isomers, the corresponding trans-isomers are also useful herein. Reference hereinafter to ethene-1,2-dicarboxy-1-phosphonic acid or salts thereof, unless otherwise specified, is intended as contemplating the cis- and trans-isomers and mixtures thereof.

Mixtures of any of the foregoing anti-calculus agents can be used in the compositions of this invention.

As used herein, "pharmaceutically acceptable salts" may refer to salts of anions or salts of cations. Suitable salts of anions include the alkali metal, e.g., sodium, potassium or lithium, the alkaline earth metal, e.g., calcium, magnesium, or strontium, stannous indium, ammonium, and substituted ammonium, e.g., mono-, di-, or triethanolammonium salts. Suitable salts of cations include the halide (for example, chloride), nitrate, sulfate, acetate, and gluconate salts.

As used herein, "water-soluble" refers to a condition of water solubility at 25°C. equal to or greater than 0.01% by weight.

Ethane-1-hydroxy-1,1-diphosphonic acid, an especially preferred anti-calculus agent, has the molecular formula $CH_3C(OH)(PO_3H_2)_2$. (According to nomenclature by radicals, the acid might also be named 1-hydroxyethylidene diphosphonic acid). It is also referred to variously as "EHDP" and etidronic acid, the former being a trademark name for the acid or its salts. The most readily crystallizable salt of this acid is obtained when three of the acid hydrogens are replaced by sodium. Preferred salts for the purpose of this invention are the trisodium hydrogen salt which has the structure:

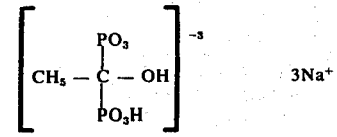

and the disodium salt.

The trisodium hydrogen salt normally crystallizes as the hexahydrate which loses some water during air-drying to yield a mixture of the hexa- and monohydrate averaging 3 to 4 molecules of water of hydration.

While any pharmaceutically acceptable salt of ethane-1-hydroxy-1,1-diphosphonic acid can be used in the practice of this invention, the tetrasodium salt, the trisodium hydrogen salt, the disodium dihydrogen salt, the monosodium trihydrogen salt, the monocalcium salt and the mixtures thereof are preferred. The other pharmaceutically acceptable salts and mixtures thereof are also suitable. These compounds can be prepared by any suitable method, however, an especially preferred method is disclosed in U.S. Pat. No.

3,400,149.

The concentration of the anti-calculus agent in the oral compositions of this invention can range from about 0.1 to about 10% by weight of the finished composition in excess of the amount which will react with the bis-biguanide compound to form an insoluble salt where such a reaction occurs. Of course, if an insoluble salt is not formed, the total amount of the anticalculus agent used is from about 0.01 to about 10% by weight. Oral compositions which in the ordinary course of usage could be accidentally ingested should contain lower concentrations of anti-calculus agent. Thus, a mouthwash in accordance with this invention preferably contains less than about 3% by weight of the finished composition in excess of any amount needed to react with the bis-biguanide compound to form an insoluble salt where such a reaction occurs, of anti-calculus agent. Dentifrice compositions, topical solutions and prophylaxis pastes, the latter to be administered professionally, can contain up to about 10% by weight, preferably from about 0.01 to about 5% by weight of the finished composition in excess of any amount needed to react with the bis-biguanide compound to form an insoluble salt where such a reaction occurs, of anti-calculus agent. If desired, one can use a lesser amount, so long as it is effective to reduce the stain.

It should be recognized that when the bis-biguanide compound and the anti-calculus agent are used simultaneously or both are incorporated into the same composition and the bis-biguanide compound is present as something other than a water-insoluble compound having a solubility in water less than the corresponding salt of the bis-biguanide with the anti-calculus agent, then an excess of the anti-calculus agent must be used to neutralize the bis-biguanide compound. Otherwise, the two will react leaving insufficient free anti-calculus agent.

The pH of the compositions of this invention is preferably maintained within the range of from about 4 to about 9. Below about 4, certain of the anti-calculus agents of this invention can damage dental enamel. Above about 9, the alkalinity becomes cosmetically undesirable and may irritate soft tissue in the mouth. The most preferred pH range is from about 6.0 to about 7.5.

In addition to the essential components of the oral compositions of this invention as described in the foregoing, such compositions can also contain carriers suitable for use in the oral cavity. Such carriers include the usual components of toothpaste, toothpowder, mouthwash, prophylaxis pastes and the like as more fully described hereinafter.

A dentifrice, especially toothpaste, is a preferred embodiment of this invention. Toothpaste compositions conventionally contain abrasive materials, sudsing agents, binders, humectants, flavoring and sweetening agents.

The abrasive should preferably be one which does not adsorb the bis-biguanide compound or the anti-calculus agent.

Suitable sudsing agents are those which are reasonably stable and form suds throughout a wide pH range, and which will not react with the bis-biguanide compound, i.e., non-soap nonionic, cationic, zwitterionic and amphoteric organic synthetic detergents.

The nonionic synthetic detergents which can be used with the oral compositions of the present invention may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to about 1,800. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine — products which may be varied in composition depending upon the balance between the hydrophobic and hydrophilic elements which is desired. For example, compounds containing from about 40 to about 80% polyoxyethylene by weight and having a molecular weight of from about 5,000 to about 11,000 resulting from the reaction of ethylene oxide groups with a hydrophobic base constituted of the raction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula, $R_{12}R_{13}R_{14}N \rightarrow O$, wherein $R_{12}$ contains an alkyl, alkenyl or monohydroxy alkyl radical of from about 8 to about 18 carbon atoms from 0 to about 10 ethylene oxide moieties, and from 0 to 1 glyceryl moiety, and $R_{13}$ and $R_{14}$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semi-polar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)tetradecylamine oxide, 2-dodecoxyethyldimethylamine oxide, 3-dodecoxy-2-hydroxypropyl-di(3-hydroxypropyl)amine oxide, dimethylhexadecylamine oxide.

5. Long chain tertiary phosphine oxides corresponding to the following general formual $R_{15}R_{16}R_{17}P \rightarrow O$, wherein $R_{15}$ contains an alkyl, alkenyl or monohydroxyalkyl radical ranging from 8 to 18 carbon atoms in chain length, from 0 to about 10 ethylene oxide moieties and from 0 to 1 glyceryl moiety and $R_{16}$ and $R_{17}$ are each alkyl or monohydroxyalkyl groups containing from 1 to 3 carbon atoms. The arrow in the formula is a conventional representation of a semipolar bond. Examples of suitable phosphine oxides are:

dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)-phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dedecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:

octadecyl methyl sulfoxide, 2-ketotridecyl methyl sulfoxide,
3,6,9-trioxaoctadecyl 2-hydroxyethyl sulfoxide,
dodecyl methyl sulfoxide,
oleyl 3-hydroxy propyl sulfoxide,
tetradecyl methyl sulfoxide,
3-methoxytridecyl methyl sulfoxide
3-hydroxytridecyl methyl sulfoxide,
3-hydroxy-4-dodecoxybutyl methyl sulfoxide.

The zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water solubilizing group, e.g., carboxy, sulfonate, sulfate, phosphate, or phosphonate. A general formula for these compounds is:

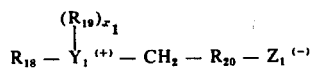

wherein $R_{18}$ contains an alkyl, alkenyl, or hydroxyalkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R_{19}$ is an alkyl or monohydroxyalkyl group containing 1 to about 3 carbon atoms; $x$ is 1 when Y is a sulfur atom and 2 when Y is a nitrogen or phosphorus atom, $R_{20}$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate
3-[P,P-diethyl-P-3,6,9-trioxatetradecoxylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]2-hydroxypentane-1-sulfate.

The cationic synthetic detergents useful in the oral compositions of the present invention can be broadly defined as quaternary ammonium compounds having 1 long alkyl chain containing from about 8 to about 18 carbon atoms such as lauryl trimethylammonium chloride; cetyl pyridinium chloride; cetyl trimethylammonium bromide; di-isobutylphenoxyethoxyethyldimethylbenzylammonium chloride; coconutalkyltrimethylammonium nitrite; cetyl pyridinium fluoride; etc. Especially preferred are the quaternary ammonium fluorides described in U.S. Pat. No. 3,535,421 incorporated by reference hereinbefore, where said quaternary ammonium fluorides have detergent properties.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, dodecyl-β-alanine, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The sudsing agent can be present in the dentifrice compositions of this invention in an amount from 0.5 to 5% by weight of the total compositions.

It is preferable to have a water-soluble fluoride compound present in an amount to give a fluoride concentration of from about 0.0025 to about 5%, preferably from about 0.005 to about 2.0%, to provide additional anticaries effectiveness. Suitable fluoride sources are disclosed in the EXAMPLES. Preferred fluorides are sodium, indium, and stannous fluorides, and sodium monofluorophosphate. The latter is especially preferred if the fluoride is present with the phosphorous-containing anticalculus agent to avoid damage to silicate fillings. It should also be remembered that the fluorides form insoluble bis-biguanide salts. U.S. Pat. No. 3,535,421 and Agricola et al.'s U.S. Pat. No. Application Ser. No. 329,783, filed Feb. 9. 1973, are incorporated herein by reference.

All parts, percentages and ratios herein are by weight unless otherwise indicated.

In preparing toothpastes, it is necessary to add some thickening material to provide a desirable consistency. Preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5 to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition.

Suitable flavoring agents include oil of wintergreen, oil of peppermint, oil of spearmint, oil of sassafras, and oil of clove. Sweetening agents which can be used include saccharin, dextrose, levulose and sodium cyclamate.

Several representative oral compositions illustrating this invention are set forth in the following examples.

EXAMPLE I

A solution was prepared containing 0.2 gram chlorhexidine [1,6-di($N_1,N_1'$-p-chlorophenyldiguanido-$N_5,N_5'$)hexane] digluconate; 1.0 gram disodium ethane-1-hydroxy-1,1-diphosphonate ("EHDP"); 0.025 gram sodium hydroxide; and 98.78 grams water, said solution having a pH of about 6.5. A precipitate forms. The resulting slurry, when used in the mouth, inhibits the formation of plaque, calculus, and caries, but with continued use, does not form the large amount of stain that would result if the "EHDP" was not present. Gingivitis is also inhibited.

EXAMPLE II

A solution was prepared containing 0.2 gram chlorhexidine digluconate; 1.0 gram of a nonionic surfactant, "Brij. 35 SP" [polyoxyethylene (23) lauryl ether]; 1.0 grams "EHDP"; 0.25 gram sodium hydroxide; and 97.78 grams water, said solution having a pH of about 6.5. The above solution inhibits the formation of plaque, calculus and caries as compared to water and when compared to 0.2% aqueous chlorhexidine solution at pH 6.5 gives less stain. Similar solutios in the pH range from about 5 to about 9 are also effective.

EXAMPLE III 0.025 gram sodium fluoride was added to 100 grams of the solution of Example II. This solution inhibits the formation of plaque and calculus, and in addition, has greater anti-caries effectiveness.

EXAMPLE IV

A solution was prepared containing 0.2 gram chlorhexidine digluconate; 1.0 gram "Victamide" (the condensation product of ammonia and phosphorus pentoxide); 1.0 gram polyoxyethylene (20) sorbitan monolaurate; 0.036 gram sodium hydroxide; and 97.76 grams water, the solution having a pH of 6.5. This solution, when used in the mouth on a regular basis, inhibits the formation of plaque, calculus and caries without excessive stain formation.

Several mouthwash compositions illustrating this invention are set forth in the following examples.

| Ingredient Ex. | V | VI | VII | VIII | IX | X | XI | XII | XIII | XIV | XV |
|---|---|---|---|---|---|---|---|---|---|---|---|
| | | | | | Percent by Weight | | | | | | |
| Glycerine | 10.0 | 10.0 | 10.0 | 10.0 | 10.0 | 10.0 | 10.0 | 10.0 | 10.0 | 10.0 | 10.0 |
| Ethyl alcohol | 16.5 | 16.5 | 16.5 | 16.5 | 16.5 | 16.5 | 16.5 | 16.5 | 16.5 | 16.5 | 16.5 |
| Polyoxyethylene (20) sorbitan monoisostearate | 1.00 | 1.00 | 1.00 | 1.50 | 1.50 | 1.50 | 1.50 | 1.50 | 1.50 | 2.00 | 2.00 |
| Sodium saccharin | .045 | .045 | .045 | .045 | .045 | .045 | .045 | .045 | .045 | .045 | .045 |
| Chlorhexidine digluconate | 0.1 | 0.2 | 1.0 | 1.5 | 1.5 | 1.0 | 0.75 | 0.70 | 0.7 | 2.4 | 1.0 |
| Flavor | .088 | .088 | .088 | .088 | .088 | .088 | .088 | .088 | .088 | .088 | .088 |
| $Mg_2$propane-1,1,3,3-tetraphosphonate | 0.5 | | | | | | | | | | |
| $Na_4$propane-2,2-diphosphonate | | 1.0 | | | | | | | | | |
| $(NH_4)$ ethane-2-carboxy-1,1-diphosphonate | | | 1.5 | | | | | | | | |
| Nonane-5,5-diphosphonic acid | | | | 1.75 | | | | | | | |
| n-pentane-1,1-diphosphonic acid | | | | | 2.0 | | | | | | |
| Ethane-2-phenyl-1,1-diphosphonic acid | | | | | | 2.25 | | | | | |
| Pent-4-ene-1-hydroxy-1,1-diphosphonic acid | | | | | | | 2.5 | | | | |
| Octadec-9-ene-1-hydroxy-1,1-diphosphonic acid | | | | | | | | 3.0 | | | |
| Methanedichlorodiphosphonic acid | | | | | | | | | 3.5 | | |
| 3-phenyl-1,1-diphosphonoprop-2-ene | | | | | | | | | | 5.0 | |
| Victamide (condensation | | | | | | | | | | | 1.5 |

|  |  |  |  |  |  | -continued |  |  |  |  |  |
|---|---|---|---|---|---|---|---|---|---|---|---|
|  |  |  |  |  |  | Percent by Weight |  |  |  |  |  |
| Ingredient | Ex. | V | VI | VII | VIII | IX | X | XI | XII | XIII | XIV | XV |
| product of ammonia and phosphorus pentoxide) |  |  |  |  |  |  |  |  |  |  |  |  |
| Sodium fluoride |  |  |  |  |  |  |  |  |  | 0.10 |  |  |
| Water |  |  |  |  |  | balance |  |  |  |  |  |  |

Adjust pH to 7.

EXAMPLE XVI

A toothpowder which constitutes yet another embodiment of this invention has the following formulation:

| Component | % by Weight |
|---|---|
| Calcium pyrophosphate | 91.30 |
| Polyoxyethylene (20) sorbitan monolaurate | 1.30 |
| Sodium saccharin | 0.25 |
| Flavoring | 1.45 |
| Chlorhexidine diacetate | 0.70 |
| Trisodium ethane-1-hydroxy-1,1-diphosphonate | 5.00 |

When diluted with water and brushed upon the teeth in the conventional manner, this composition has a pH of approximately 7.0. The composition retards the formation of plaque, calculus, and caries without excessive staining.

The trisodium ethane-1-hydroxy-1,1-diphosphonate employed in the above formulation can be replaced by an equimolar amount of dipotassium ethane-1-amino-1,1-diphosphonate; dimagnesium ethane-2-carboxy-1,1-diphosphonate; phenylaminomethanediphosphonic acid; or N,N-dimethylaminomethanediphosphonic acid with substantially equivalent results.

EXAMPLE XVII

A prophylaxis paste for use in the dental office for removal of stains and polishing the tooth surface after mechanical removal of calculus is formulated as follows:

| Component | Parts by Weight |
|---|---|
| Composition A: |  |
| Navajo pumice | 77.1 |
| TiO₂ | 4.0 |
| Glycerine | 17.757 |
| Hydroxyethylcellulose | .222 |
| Sodium saccharin | .326 |
| Methanedibromodiphosphonic acid | 2.5 |
| Composition B: |  |
| Chlorhexidine digluconate | 2.7 |
| Water | 87.00 |

Immediately prior to use 5.5 gm. of composition A are mixed with composition B to attain the desired texture and adjusted to pH 7.0. The paste is then applied to the tooth surfaces with a rubber prophylactic cup in the conventional manner. This composition inhibits the formation of plaque, calculus, and caries without adverse effects of stain formation.

The methanedibromodiphosphonic acid of this example can be replaced by an equimolar amount of N-(2-hydroxyethyl)aminomethanediphosphonic acid; bis(triethanolammonium) N-acetylaminomethanediphosphonate; dicalcium aminomethanediphosphonate; diethanolammonium methanehydroxydiphosphonate; or tris(monoethanolammonium) nonane-1,1-diphosphonate with comparable results.

EXAMPLE XVIII

Two groups of subjects, 20 persons per group, were recruited. These subjects each wore at least one complete denture. All subjects were given a 0.2% aqueous chlorhexidine solution. Half the subjects received a placebo toothpaste. The other half received a similar toothpaste containing 3% EHDP. Instructions were: Before retiring, brush your denture with the paste provided; rinse it; immerse it for 15 minutes in the denture soak (0.2% chlorhexidine); rinse, and replace in the mouth.

Stain development was evaluated by photographing the dentures at the start and after one week. The photographs were graded against an established scale from 0 for no stain to 4 for intense stain. The average gains in stain per person were computed: Gain with placebo paste — 0.34; gain with EHDP paste — 0.14. The stain was less with the etidronate paste.

EXAMPLE XIX

Two groups of 16 subjects with natural teeth received dental prophylaxes, and were given a 0.1% aqueous chlorhexidine mouthwash; a placebo or 3.0% EHDP toothpaste. The subjects were asked to use the mouthwash once daily, and to brush with the toothpaste immediately after use of the mouthwash. Stain was graded on the teeth by a dentist, and was significantly less when the EHDP paste was used: Gain with placebo paste, per person — 0.18; Gain with EHDP paste, per person — 0.10.

If desired, sodium fluoride or sodium monofluorophosphate can be added to the EHDP paste to provide additional anticaries action.

If desired, sodium fluoride or sodium monofluorophosphate can be added to the chlorhexidine solution. This will result in some formation of an insoluble chlorhexidine salt although the fluoride ion remaining will be effective to reduce the incidence of caries.

EXAMPLE XX

When in any of the previous examples the following anti-calculus agents are substituted, either wholly or in part, for the specified anti-calculus agents, substantially equivalent results are obtained in that the formulas provide antiplaque, anti-calculus, and anti-caries activity without staining the oral surfaces: disodium salt of ethane-1,2-dicarboxy-1,2-diphosphonic acid; dipotassium salt of ethane-1,2-dicarboxy-1,2-dihydroxy-1,2-diphosphonic acid; the monocalcium salt of ethene-1,2-dicarboxy-1-phosphonic acid; the mono-magnesium salt of ethane-1,2-dicarboxy-1-hydroxy-1,1-diphosphonic acid; the di(triethanolammonium) salt of ethane-1,2-dicarboxy-1,2-diphosphonic acid rather than the disodium salt of ethane-1,2-dicarboxy-1,2-diphosphonic acid; diammonium salt of ethane-1,2-dicarboxy-1,2-diphosphonic acid; monocalcium salt of ethane-1,2-dicarboxy-1,2-dihydroxy-1,2-diphosphonic acid; distannous salt of ethane-1,2-dicarboxy-1-hydroxy-1,2-diphosphonic acid; indium salt of ethene-1,2-dicarboxy-1-phosphonic acid; triammonium salt of ethane-1,2-dicarboxy-1,2-dihydroxy-1,2-diphosphonic acid; trisodium salt of ethene-1,2-dicarboxy-1-phosphonic acid; distannous salt of ethane-1,2-dicarboxy-1,2-diphosphonic acid; hexasodium salt of cyclic tetraphosphonic acid; trisodium salt of methane cyclohexylhydroxydiphosphonic acid; diammonium salt of methanecyclobutylhydroxydiphosphonic acid; monocalcium salt of methanecyclopentylhydroxydiphosphonic acid; distannous salt of methanecycloheptylhydroxydiphosphonic acid; indium salt of methanecyclooctylhydroxydiphosphonic acid; triammonium salt of methanecyclononylhydroxydiphosphonic acid; trisodium salt of methanecyclodecylhydroxydiphosphonic acid; distannous salt of methanecyclohexylhydroxydiphosphonic acid; methanecycloalkylhydroxydiphosphonic acid; tris(1-phosphonoethyl)amine; tetrasodium salt of tris(2-phosphono-2-propyl) amine; dipotassium salt of bis(phosphonomethyl)-1-phosphonoethyl amine; monocalcium salt of bis(phosphonomethyl)-2-phosphono-2-propyl amine; monomagnesium salt of bis(1-phosphonoethyl)phosphonomethyl amine; distannous salt of bis(2-phosphono-2-propyl)phosphonomethyl amine; Victamide; zinc phenolsulfonate; sodium 8-hydroxyquinoline; sodium lactate; ammonium citrate, water-soluble sodium poly(maleic acid), water-soluble sodium poly(itaconic acid), water-soluble sodium poly(methylenemalonic acid), sodium pyrophosphate, a water-soluble copolymer of 70 mole percent potassium polymaleate and 30 mole percent polymaleic acid, a water-soluble copolymer of sodium polymaleic acid and polyethylene (1:1 on a molar basis), a water-soluble polymer of sodium poly(itaconate-aconitate) (1:1 on a molar basis), N-methyl-N-dodecyl-N-(2-hydroxyethyl)-N-benzyl ammonium chloride, N-methyl-N-(2-hydroxydodecyl)-N-(2-hydroxyethyl)-N-benzyl ammonium chloride, N-methyl-N-(2-hydroxytetradecyl)-N-(2-hydroxyethyl)-N-benzyl ammonium chloride, diisobutylphenoxy-ethoxy-ethyldimethyl benzyl ammonium chloride, disodium tripolyphosphate, lanthanum chloride, cerium nitrate, and sodium phytate. Mixtures of the above anti-calculus agents can also be used, and substantially equivalent results will be obtained.

EXAMPLE XXI

Another toothpaste prepared in accordance with this invention has the following composition:

| Component | % by Weight |
|---|---|
| Precipitated urea/formaldehyde condensate (abrasive) | 31.00 |
| Sorbitol (70% aqueous solution) | 6.25 |
| Glycerine | 18.00 |
| Polyoxyethylene (20) sorbitan monoisostearate | 1.50 |
| Hydroxyethylcellulose | 1.15 |
| Magnesium aluminum silicates | 0.40 |
| Sodium saccharin | 0.04 |
| Flavoring | 0.95 |
| Methanediphosphonic acid | 1.50 |
| Sodium monofluorophosphate | 3.00 |
| Sodium fluoride | 0.01 |
| Chlorhexidine digluconate | 1.50 |
| Water | balance |

Mole ratio polyphosphonate/fluoride 2.4
pH adjusted to 7.5 with 5N NaOH

This composition is effective in retarding the formation of dental calculus when used in a conventional manner. Post eruptive maturation of dental enamel is not impeded by this composition; nor are mature dental enamel or silicate filling materials adversely effected thereby. This composition also inhibits plaque and caries.

EXAMPLES XXII & XXIII

| Component | % by Weight | |
|---|---|---|
|  | Example XXII | Example XXIII |
| Chlorhexidine digluconate | 0.2 | 0.2 |
| "EHDP" | 1.0 |  |
| Victamide |  | 1.0 |
| Brij 35 SP | 1.0 | 1.0 |
| Ethanol | 12.0 | 12.0 |
| Glycerol | 6.0 | 6.0 |
| Water | balance | balance |

When in the above examples the following water-soluble fluoride agents are substituted, either wholly or in part, for the sodium fluoride, substantially equivalent results are obtained in that the formulas provide additional anti-caries activity: stannous fluoride; potassium fluoride, lithium fluoride, cesium fluoride, ammonium fluoride, aluminum fluoride, cupric fluoride, indium fluoride, stannous fluorozirconate, lead fluoride, ferric fluoride, nickel fluoride, palladium fluoride, silver fluoride, zinc fluoride, zirconium fluoride, hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolaminoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, $\Delta^{8,9}$-octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N'-dilaurylethylene-diammonium difluoride, N-cetylpyridinium fluoride, N:N-dilauryl-morpholinium fluoride, N-myristyl-N-ethylmorpholinium fluoride, N-(octylaminocarbonylethyl)-N-benzyl-dimethylammonium fluoride, N-($\beta$-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-eicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, and mixtures thereof in, e.g., 1:1 proportions.

When in the above examples the following surface-active agents are inserted in an amount of from about 1 to 2% as an additional ingredient, substantially equivalent results are obtained, except that the compositions have enhanced detergency effects: polypropylene glycol (M.W. 1700) polyoxyethylene (M.W. 1500); polyoxypropylene (70) ethylenediamine polyoxyethylene (100); coconut alcohol polyoxyethylne (20); dimethyldodecylamine oxide; oleyldi(2-hydroxyethyl)amine oxide; dimethyloctylamine oxide; dimethyldecylamine oxide; dimethyltetradecylamine oxide; 3,6,9-trioxaheptadecyldiethylamine oxide; di(2-hydroxyethyl)tetradecylamine oxide; 2-dodecoxyethyldimethylamine oxide; 3-dodecoxy-2-hydroxypropyldi(3-hydroxypropyl)amine oxide; dimethylhexadecylamine oxide; dodecyldimethylphosphine oxide; tetradecyldimethylphosphine oxide; tetradecylmethylethylphosphine oxide; 3,6,9-trioxaoctadecyldimethylphosphine oxide; cetyldimethylphosphine oxide; 3-dodecoxy-2-hydroxypropyldi(2-hydroxyethyl)phosphine oxide; stearyldimethylphosphine oxide; cetylethylpropylphosphine oxide; oleyldiethylphosphine oxide; dodecyldiethylphosphine oxide; tetradecyldiethylphosphine oxide; dodecyldipropylphosphine oxide; dodecyldi(hydroxymethyl)phosphine oxide; dodecyldi(2-hydroxyethyl)phosphine oxide; tetradecylmethyl-2-hydroxypropylphosphine oxide; oleyldimethylphosphine oxide; 2-hydroxydodecyldimethylphosphine oxide; octadecyl methyl sulfoxide; 2-ketotridecyl methyl sulfoxide; 3,6,9-trioxaoctadecyl 2-hydroxyethyl solfoxide; dodecyl methyl sulfoxide; oleyl 3-hydroxypropyl sulfoxide; tetradecyl methyl sulfoxide; 3-methoxytridecyl methyl sulfoxide; 3-hydroxytridecyl methyl sulfoxide; 3-hydroxy-4-dodecoxybutyl methyl sulfoxide; 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-p-3,6,9-trioxatetradecoxylphosphonio]-2-hydroxypropane-1-phosphate; 3-[N,N-dipropyl-N-3-dodecoxy-2-hydroxypropylammonio[-propane-1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl) ammonio[-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; 5-[N,N-di(3-hydroxypropyl)-N-hexadecylammonio]2-hydroxypentane-1-sulfate; dodecyltrimethylammonium chloride; nonylbenzylethyldimethylammonium nitrate; tetradecylpyridinium bromide; octadecylbutylpropylmethylphosphonium nitrate; decyldimethylsulfonium chloride; (hexylphenyl)dimethylbenzylammonium fluoride; eicosyldimethylbenzylphosphonium chloride; coconutalkylmethylmorpholinium nitrate; octadecylmethylbenzylsulfonium sulfate; laurylpyridinium chloride; laurylpyridinium bromide; laurylpyridinium bisulfate; laurylpyridinium-5-chloro-2-mercaptobenzothiazole; laurylpicolinium-p-toluenesulfonate; tetradecylpyridinium bromide; cetylpyridinium chloride; cetylpyridinium bromide; laurylisoquinolinium bromide; laurylisoquinolinium saccharinate; alkylisoquinolinium bromide; N-cetyl-N-ethyl-morpholinium ethosulfate; benzalkonium chloride; monoquaternaries $R_4N^+X^-$ (one R group is fatty); octadecyltrimethylammonium chloride; coconut alkyl trimethylammonium chloride; dodecylbenzyltri(octyldecyl)ammonium chloride; monoquaternaries $R_4N^+X^-$ (two R groups are fatty); dihexadecyldimethylammonium chloride; di-coconut alkyl dimethylammonium chloride; monoquaternaries $R_4N^+X^-$ (three R groups are fatty); tri(hydrogenated tallow) methylammonium chloride; distilled tallow amine acetate; diamine acetates; N-oleyl propylene diamine monoacetate; condensation product of octyl phenol with 15 moles of ethylene oxide per mole of octyl phenol; dimethyldodecylamine oxide; dodecyldimethylphosphine oxide; tetradecyl methyl sulfoxide; 3-(N,N-dimethyl-N-hexdecylammonio)propane-1-sulfonate; 3-dodecylaminopropionate; and dodecyl-$\beta$-alanine.

When in the above examples, the following bisbiguanide compounds are substituted, either wholly or in part (50%) for the preferred chlorhexidine digluconate, substantially equivalent results are obtained in that plaque, calculus, gingivitis and caries are inhibited with reduced staining as compared to the use of the bisbiguanide compounds alone: 1,6-bis-(2-ethylhexylbiguanidohexane)dihydrochloride; 1,6-di-($N_1$, $N_1'$-phenyldiguanido-$N_5$, $N_5'$)-hexane tetrahydrochloride; 1,6-di-($N_1$, $N_1'$-phenyl-$N_1$, $N_1'$-methyldiguanido-$N_5$, $N_5'$)-hexane dihydrochloride; 1,6-di($N_1$, $N_1'$-o-chlorophenyldiguanido-$N_5$, $N_5'$)-hexane dihydrochloride; 1,6-di($N_1$, $N_1'$-2,6-dichlorophenyldiguanido-$N_5$, $N_5'$)hexane dihydrochloride; 1,6-di[$N_1$, $N_1'$-$\beta$-(p-methoxyphenyl)diguanido-$N_5$, $N_5'$]-hexane dihydrochloride; 1,6-di($N_1$, $N_1'$-$\alpha$-methyl-$\beta$-phenyldiguanido-$N_5$, $N_5'$)-hexane dihydrochloride; 1,6-di($N_1$, $N_1'$-p-nitrophenyldiguanido-$N_5$, $N_5'$)hexane dihydrochloride; $\omega$:$\omega'$-di-($N_1$, $N_1'$-phenyldiguanido-$N_5$, $N_5'$)-di-n-propylether dihydrochloride; $\omega$:$\omega'$-di($N_1$, $N_1'$-p-chlorophenyldiguanido-$N_5$, $N_5'$)-di-n-propylether tetrahydrochloride; 1,6-di($N_1$, $N_1'$-2,4-dichlorophenyldiguanido-$N_5$, $N_5'$)hexane tetrahydrochloride; 1,6-di($N_1$, $N_1'$-p-methylphenyldiguanido-$N_5$, $N_5'$)hexane dihydrochloride; 1,6-di($N_1$, $N_1'$-2,4,5-trichlorophenyldiguanido-$N_5$, $N_5'$)hexane tetrahydrochloride; 1,6-di[$N_1$, $N_1'$-$\alpha$-(p-chlorophenyl)ethyldiguanido-$N_5$, $N_5'$[hexane dihydrochloride; $\omega$:$\omega'$-di($N_1$, $N_1'$-p-chlorophenyldiguanido-$N_5$, $N_5'$)m-xylene dihydrochloride; 1,12-di-($N_1$, $N_1'$-p-chlorophenyldiguanido-$N_5$, $N_5'$)dodecane dihydrochloride; 1,10-di($N_1$, $N_1'$-phenyldiguanido-$N_5$, $N_5'$)-decane tetrahydrochloride; 1,12-di($N_1$, $N_1'$-phenyldiguanido-$N_5$, $N_5'$)dodecane tetrahydrochloride; 1,6-di($N_1$, $N_1'$-o-chlorophenyldiguanido-$N_5$, $N_5'$)hexane dihydrochloride; 1,6-di($N_1$,$N_1'$-p-chlorophenyldiguanido-$N_5$, $N_5'$)-hexane tetrahydrochloride; ethylene bis(1-tolyl biguanide); ethylene bis(p-tolyl biguanide); ethylene bis(3,5-dimethylphenyl biguanide); ethylene bis(p-tert-amylphenyl biguanide); ethylene bis(nonylphenyl biguanide); ethylene bis(phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenyl biguanide); ethylene bis(mixed amyl naphthyl biguanide); N-butyl ethylene bis(phenyl biguanide); trimethylene bis(o-tolyl biguanide); N-butyl trimethylene bis(-phenylbiguanide); tetramethylene bis(1-tolyl biguanide); the specific compounds disclosed in U.S. Pat. No. 2,863,919, Birtwell et al., (Dec. 9, 1958), said patent being incorporated herein by reference; the specific compounds disclosed in U.S. Pat. No. 3,468,898, Cutler et al., (Sept. 23, 1969), said patent being incorporated herein by reference; and the corresponding pharmaceutically acceptable salts of all of the above such as the acetates; gluconates; hydrochlorides; hydrobromides; citrates; bisulfites, fluorides, polymaleates, N-coconutalkyl sarcosinates, phosphites, hypophosphites, perfluorooctanoates, silicates, sorbates, salicylates, maleates, tartrates, fumarates, ethylenediaminotetraacetates, iminodiacetates, cinnamates, thiocyanates, arginates, pyromellitates, tetracarboxybutyrates, benzoates, glutarates, monofluorophosphates, and perfluoropropionates.

What is claimed is:

1. An oral composition effective in inhibiting the formation of plaque, caries and calculus comprising:

A. from about 0.01 to about 2.5% by weight of a bis-biguanide compound having the generic formula:

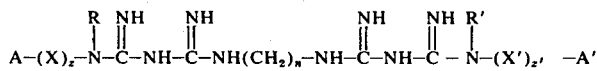

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof;

B. from about 0.01 to about 10% by weight of an anti-calculus compound in excess over that which reacts with said bis-biguanide compound to form an insoluble salt where such reaction occurs, said anti-calculus compound being zinc phenolsulfonate;

c. balance, a carrier which is suitable for use in the oral cavity.

2. An oral composition effective in inhibiting the formation of plaque, caries and calculus comprising:

A. from about 0.01 to about 2.5% by weight of a bis-biguanide compound having the generic formula:

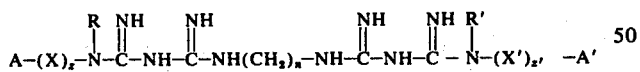

wherein A and A' each represent either (1) a phenyl radical which can contain as a substituent up to two alkyl or alkoxy groups containing about 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof;

B. from about 0.01 to about 10% by weight of an anti-calculus compound in excess over that which reacts with said bis-biguanide compound to form an insoluble salt where such reaction occurs, said anti-calculus compound being selected from the group consisting of 8-hydroxyquinoline and pharmaceutically acceptable salts of 8-hydroxyquinoline;

C. balance, a carrier which is suitable for use in the oral cavity.

3. An oral composition effective in inhibiting the formation of plaque, caries and calculus comprising:

A. from about 0.01 to about 2.5% by weight of a bis-biguanide compound having the generic formula:

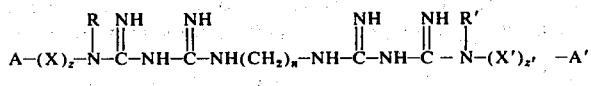

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof;

B. from about 0.01 to about 10% by weight of an anti-calculus compound in excess over that which reacts with said bis-biguanide compound to form an insoluble salt where such reaction occurs, said anti-calculus compound being selected from the group consisting of: (1) water-soluble pharmaceutically acceptable salts of homopolymers of aliphatic polycarboxylic acids having the following empirical formula:

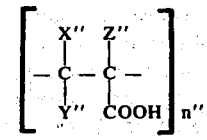

wherein X'', Y'', and Z'' are each selected from the group consisting of hydrogen, methyl, carboxyl, and carboxymethyl; at least one of X'', Y'' and Z'' being selected from the group consisting of carboxyl and carboxymethyl, provided that X'' and Y'' can be carboxymethyl only when Z'' is selected from carboxyl and carboxymethyl; wherein only one of X'', Y'' and Z'' can be methyl, and wherein $n''$ is an integer of from 3 to about 5,000;

2. water-soluble pharmaceutically acceptable salts of copolymers of at least two of polycarboxylic acids having the emperical formula of (1);

3. water-soluble, pharmaceutically acceptable salts of copolymers having the following general formula:

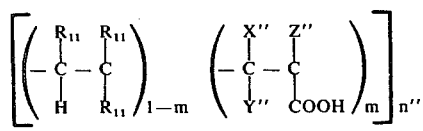

wherein each $R_{11}$ is selected from the group consisting of hydrogen, methyl, carboxyl, carboxymethyl and carboxyethyl; wherein only one $R_{11}$ is methyl; wherein m is at least 45 mole percent of the copolymer; and wherein $X''$, $Y''$, $Z''$ and $n''$ are selected as in (1):

C. balance, a carrier which is suitable for use in the oral cavity.

4. An oral composition effective in inhibiting the formation of plaque, caries and calculus comprising:
A. from about 0.01 to about 2.5% by weight of a bis-biguanide compound having the generic formula:

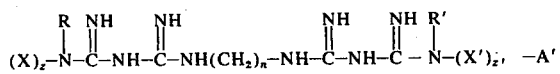

wherein A and A' each represent either (1) a phenyl radical which can contain as a substituent up to two alkyl or alkoxy groups containing from 1 to about 4 carbon atoms; a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof;
B. from about 0.01 to about 10% by weight of an anti-calculus compound in excess over that which reacts with said bis-biguanide compound to form an insoluble salt where such reaction occurs, said anti-calculus agent being selected from the group consisting of polyphosphates of the general formula $H_{a+2} P_a O_{3a+1}$ where a is an integer of from 2 to about 30 and pharmaceutically acceptable salts thereof; and
C. balance, a carrier which is suitable for use in the oral cavity.

5. An oral composition effective in inhibiting the formation of plaque, caries and calculus comprising:
A. from about 0.01 to about 2.5% by weight of a bis-biguanide compound having the generic formula:

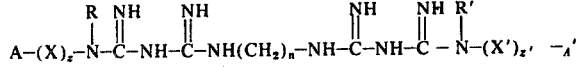

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof; and a composition comprising:
B. from about 0.01 to about 10% by weight of an anti-calculus compound in excess over that which reacts with said bis-biguanide compound to form an insoluble salt where such reaction occurs, said anti-calculus agent being a pharmaceutically acceptable salt of a rare earth metal.
C. balance, a carrier which is suitable for use in the oral cavity.

6. An oral composition effective in inhibiting the formation of plaque, caries and calculus comprising:
A. from about 0.01 to about 2.5% by weight of a bis-biguanide compound having the generic formula:

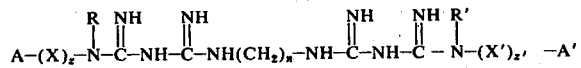

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof;
B. from about 0.01 to about 10% by weight of an anti-calculus compound in excess over that which reacts with said bis-biguanide compound to form an insoluble salt where such reaction occurs, said anti-calculus agent being selected from the group consisting of phytic acid and pharmaceutically acceptable salts thereof; and
C. balance, a carrier which is suitable for use in the oral cavity.

7. An oral composition effective in inhibiting the formation of plaque, caries and calculus comprising:
A. from about 0.01 to about 2.5% by weight of a bis-biguanide compound having the generic formula:

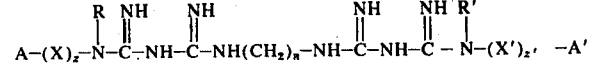

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof;

B. from about 0.01 to about 10% by weight of an anti-calculus compound in excess over that which reacts with said bis-biguanide compound to form an insoluble salt where such reaction occurs, said anti-calculus compound being selected from the group consisting of compounds of the following general formulae and pharmaceutically acceptable salts thereof:

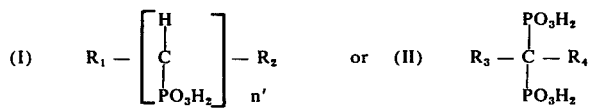

wherein $R_1$ and $R_2$ are hydrogen or $CH_2OH$; $n'$ is an integer of from 3 to 10; $R_3$ is hydrogen, alkyl containing from 1 to about 20 carbon atoms, alkenyl containing from 2 to about 20 carbon atoms, phenyl, naphthyl, phenylethenyl, benzyl, halogen, amino, dimethylamino, diethylamino, N-hydroxy-N-ethylamine, acetylamino, $-CH_2COOH$, $-CH_2PO_3H_2$, $-CH(PO_3H_2)$ (OH) or $-CH_2CH(PO_3H_2)_2$; and $R_4$ is hydrogen, lower alkyl, amino, benzyl, halogen, hydroxyl, $-CH_2COOH$, $-CH_2PO_3H_2$, or $-CH_2CH_2PO_3H_2$;

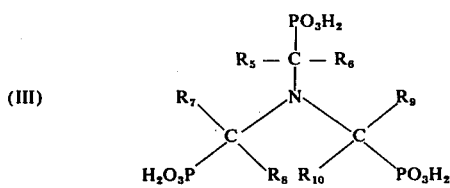

wherein $R_5$, $R_6$, $R_7$, $R_8$, $R_9$ and $R_{10}$ are each hydrogen or lower alkyl;

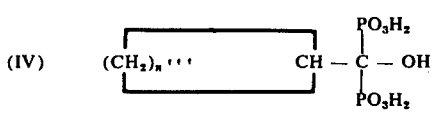

wherein $n'''$ is an integer from 3 to 9;

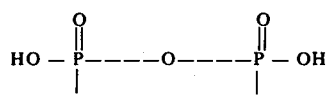

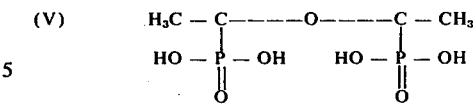

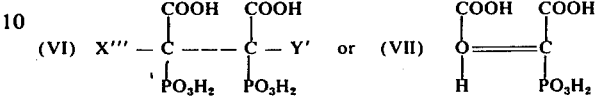

wherein $X'''$ and $Y'$ are each hydrogen or hydroxy; or the condensation products of ammonia and phosphorus pentoxide, comprising the compounds

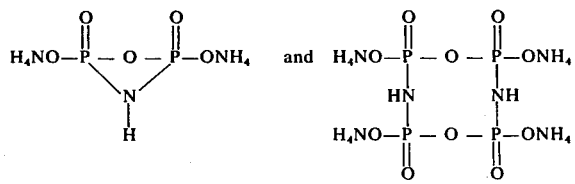

; and

C. balance, a carrier which is suitable for use in the oral cavity.

8. The composition of claim 7 having a pH within the range of from about 4 to about 9.

9. The composition of claim 7 containing a water-soluble source of fluoride in a quanity sufficient to provide fluoride in an amount from about 0.0025 to about 5.0% as $F^-$.

10. The composition of claim 7 containing from about 0.05 to about 1.2% by weight of the bis-biguanide compound and from about 0.01% to about 5% by weight of the anti-calculus compound, and the pH of the composition is from about 6 to about 7.5.

11. The composition of claim 7 wherein the bis-biguanide compound is [1,6-di($N_1$,$N_1'$-p-chlorophenyldiguanido-$N_5$,$N_5'$)hexane]digluconate, and the anti-calculus compound is disodium ethane-1-hydroxy-1,1-diphosphonate.

12. The composition of claim 7 wherein the composition is a dentifrice, the carrier is an abrasive present at a level of from 31 to 91.6% and the composition additionally contains from about 0.5 to 5.0 % of a sudsing agent.

13. The composition of claim 7 wherein the bis-biguanide compound is derived from a pharmaceutically acceptable salt selected from the group consisting of the chloride, acetate, and gluconate salts.

14. The composition of claim 7 wherein $A - (X)_z$ is an ethylhexyl group and n is 6.

15. The composition of claim 7 wherein A and A' are each p-chlorophenyl groups, $z$ and $z'$ are O, and $n$ is 6.

16. The process of treating the oral cavity with a composition comprising:

A. from about 0.01 to about 2.5% by weight of a bis-biguanide compound having the generic formula:

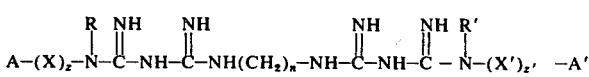

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof; and a composition comprising:
B. from about 0.01 to about 10% by weight of an anti-calculus compound in excess over that which reacts with said bis-biguanide or compound to form an insoluble salt where such reaction occurs, said anti-calculus compound being zinc phenolsulfonate.

17. The process of claim 16 wherein the two compositions are the same composition.

18. The process of claim 16 wherein the oral cavity is treated first with the composition containing the bis-biguanide compound and then with the composition containing the anti-calculus compound.

19. The process of treating the oral cavity with a composition comprising:
A. from about 0.01 to about 2.5% by weight of a bis-biguanide compound having the generic formula:

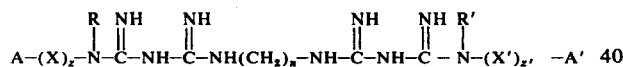

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof; and a composition comprising:
B. from about 0.01 to about 10% by weight of an anti-calculus compound in excess over that which reacts with said bis-biguanide compound to form an insoluble salt where such reaction occurs, said anti-calculus compound being selected from the group consisting of 8-hydroxyquinoline and pharmaceutically acceptable salts of 8-hydroxyquinoline.

20. The process of claim 19 wherein the two compositions are the same composition.

21. The process of claim 19 wherein the oral cavity is treated first with the composition containing the bis-biguanide compound and then with the composition containing the anti-calculus compound.

22. The process of treating the oral cavity with a composition comprising:
A. from about 0.01 to about 2.5% by weight of a bis-biguanide compound having the generic formula:

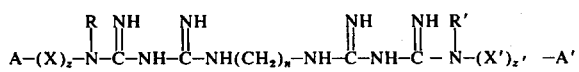

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof; and a composition comprising:
B. from about 0.01 to about 10% by weight of an anti-calculus compound in excess over that which reacts with said bis-biguanide compound to form an insoluble salt where such reaction occurs, said anti-calculus compound being selected from the group consisting of: (1) water-soluble pharmaceutically acceptable salts of homopolymers of aliphatic polycarboxylic acids having the following empirical formula:

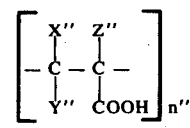

wherein X'', Y'', and Z'' are each selected from the group consisting of hydrogen, methyl, carboxyl, and carboxymethyl; at least one of X'', Y'' and Z'' being selected from the group consisting of carboxyl and carboxymethyl, provided that X'' and Y'' can be carboxymethyl only when Z'' is selected from carboxyl and carboxymethyl; wherein only one of X'', Y'' and Z'' can be methyl, and wherein n'' is an integer of from 3 to about 5,000;
2. water-soluble pharmaceutically acceptable salts of copolymers of at least two of polycarboxylic acids having the emperical formula of (1);
3. water-soluble, pharmaceutically acceptable salts of copolymers having the following general formula:

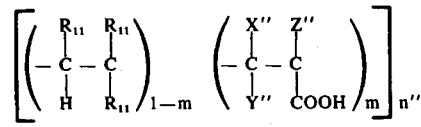

wherein each $R_{11}$ is selcted from the group consisting of hydrogen, methyl, carboxyl, carboxymethyl and carboxyethyl; wherein only one $R_{11}$ is methyl; wherein m is at least 45 mole percent of the copolymer; and wherein $X''$, $Y''$, $Z''$ and $n''$ are selected as in (1).

23. The process of claim 22 wherein the two compositions are the same composition.

24. The process of claim 22 wherein the oral cavity is treated first with the composition containing the bis-biguanide compound and then with the composition containing the anti-calculus compound.

25. The process of treating the oral cavity with a composition comprising:
A. from about 0.01 to about 2.5% by weight of a bis-biguanide compound having the generic formula:

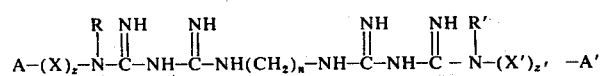

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof; and a composition comprising:
B. from about 0.01 to about 10% by weight of an anti-calculus compound in excess over that which reacts with said bis-biguanide compound to form an insoluble salt where such reaction occurs, said anti-calculus compound being selected from the group consisting of polyphosphates of the general formula $H_{a+2} P_a O_{3a+1}$ wherein a is an integer of from 2 to about 30 and pharmaceutically acceptable salts thereof.

26. The process of claim 25 wherein the two compositions are the same composition.

27. The process of claim 25 wherein the oral cavity is treated first with the composition containing the bis-biguanide compound and then with the composition containing the anti-calculus compound.

28. The process of treating the oral cavity with a composition comprising:
a. from about 0.01 to about 2.5% by weight of a bis-biguanide compound having the generic formula:

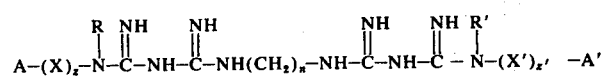

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof; and a composition comprising:
B. from about 0.01 to about 10% by weight of an anti-calculus compound in excess over that which reacts with said bis-biguanide compound to form an insoluble salt where such reaction occurs, said anti-calculus agent being a pharmaceutically acceptable salt of a rare earth metal.

29. The process of claim 28 wherein the two compositions are the same composition.

30. The process of claim 28 wherein the oral cavity is treated first with the composition containing the bis-biguanide compound and then with the composition containing the anti-calculus compound.

31. The process of treating the oral cavity with a composition comprising:
A. from about 0.01 to about 2.5% by weight of a bis-biguanide compound having the generic formula:

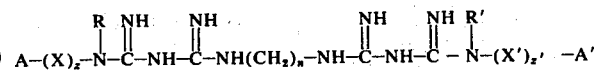

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof;
B. from about 0.01 to about 10% by weight of an anti-calculus compound in excess over that which reacts with said bis-biguanide compound to form an insoluble salt where such reaction occurs, said anti-calculus compound being selected from the group consisting of phytic acid and pharmaceutically acceptable salts thereof.

32. The process of claim 31 wherein the two compositions are the same composition.

33. The process of claim 31 wherein the oral cavity is treated first with the composition containing the bis-biguanide compound and then with the composition containing the anti-calculus compound.

34. The process of treating the oral cavity with a composition comprising:

A. from about 0.01 to about 2.5% by weight of a bis-biguanide compound having the generic formula:

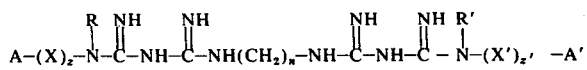

wherein A and A' each represent either (1) a phenyl radical which can contain as a substituent up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl or naphthyl moieties; or the pharmaceutically acceptable salts thereof; and a composition comprising:

B. from about 0.01 to about 10% by weight of an anti-calculus compound in excess over that which reacts with said bis-biguanide compound to form an insoluble sale where such reaction occurs, said anti-calculus compound being selected from the group consisting of compounds of the following general formulae and pharmaceutically acceptable salts thereof:

(I) 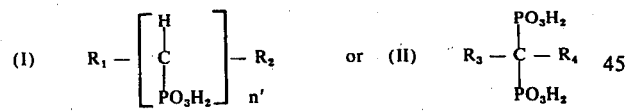

wherein $R_1$ and $R_2$ are hydrogen or $CH_2OH$; $n'$ is an integer of from 3 to 10; $R_3$ is hydrogen, alkyl containing from 1 to about 20 carbon atoms, alkenyl containing from 2 to about 20 carbon atoms, phenyl, naphthyl, phenylethenyl, benzyl, halogen, amino, dimethylamino, diethylamino, N-hydroxy-N-ethylamine, acetylamino, $-CH_2COOH$, $-CH_2PO_3H_2$, $-CH(PO_3H_2)$ (OH) or $-CH_2CH(PO_3H_2)_2$; and $R_4$ is hydrogen, lower alkyl, amino, benzyl, halogen, hydroxyl, $-CH_2COOH$, $-CH_2PO_3H_2$, or $-CH_2CH_2PO_3H_2$;

(III) 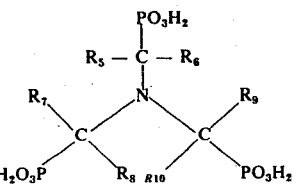

wherein $R_5$, $R_6$, $R_7$, $R_8$, $R_9$ and $R_{10}$ are each hydrogen or lower alkyl;

(IV) 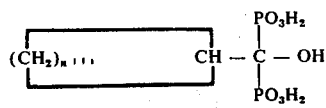

wherein $n'''$ is an integer from 3 to 9;

(V) 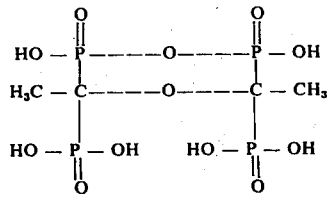

(VI) 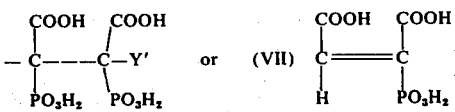 or (VII)

wherein $X'''$ and $Y'$ are each hydrogen or hydroxy; or the condensation products of ammonia and phosphorous pentoxide, comprising the compounds

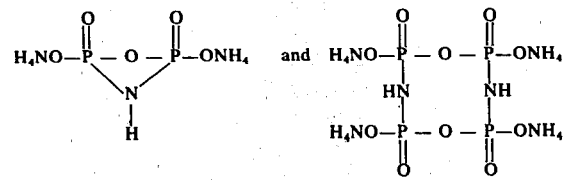

35. The process of claim 34 wherein the two compositions are the same composition.

36. The process of claim 34 wherein the oral cavity is treated first with the composition containing the bis-biguanide compound and then with the composition containing the anti-calculus compound.

* * * * *